(12) United States Patent
Blandino et al.

(10) Patent No.: US 7,939,624 B2
(45) Date of Patent: May 10, 2011

(54) PEPTIDE ABLE TO BREAK THE M-P53/P63, M-P53/P73 AND M-P53/RESPECTIVE ISOFORM PROTEINS COMPLEX FORMED IN THE TUMOR CELLS AND USES THEREOF IN THE PHARMACOLOGICAL FIELD

(75) Inventors: Giovanni Blandino, Rome (IT); Gennaro Citro, Rome (IT); Alessandra Verdina, Rome (IT); Rossella Maria Galati, Rome (IT)

(73) Assignee: Instituti Fisioterapici Ospitalieri, Rome (IT)

( * ) Notice: Subject to any disclaimer, the term of this patent is extended or adjusted under 35 U.S.C. 154(b) by 963 days.

(21) Appl. No.: 11/719,169

(22) PCT Filed: Nov. 14, 2005

(86) PCT No.: PCT/IB2005/003395
§ 371 (c)(1),
(2), (4) Date: May 11, 2007

(87) PCT Pub. No.: WO2006/054138
PCT Pub. Date: May 26, 2006

(65) Prior Publication Data
US 2009/0181418 A1    Jul. 16, 2009

(30) Foreign Application Priority Data
Nov. 19, 2004   (IT) .............................. MI2004A2227

(51) Int. Cl.
*C07K 5/00* (2006.01)
*C07K 7/00* (2006.01)
*C07K 14/00* (2006.01)
*C07K 16/00* (2006.01)
*C07K 17/00* (2006.01)
*A61K 38/04* (2006.01)
*A61K 38/06* (2006.01)

(52) U.S. Cl. .......................... 530/300; 530/327; 530/328
(58) Field of Classification Search ........................ None
See application file for complete search history.

(56) References Cited

FOREIGN PATENT DOCUMENTS

| WO | WO 97/28186 | * | 8/1997 |
| WO | 9851350 A1 | | 11/1998 |
| WO | WO 99/50287 | * | 10/1999 |
| WO | 9966946 A1 | | 12/1999 |
| WO | 03025010 A2 | | 3/2003 |

* cited by examiner

*Primary Examiner* — Marcela M Cordero Garcia
(74) *Attorney, Agent, or Firm* — Pearne & Gordon LLP

(57) ABSTRACT

The object of the present invention is the identification of a group of peptides able to break the interaction between the mutated protein p53 (hereinafter m-p53) and the proteins p63, p73 and the relative isoform proteins (hereinafter p63, p73 and p-isoforms) in the m-p53/p63, m-p53/p73 and m-p53/p-isoforms proteinic complex that has formed in the nucleus of tumor cells. Furthermore, the present invention relates to a method for causing the breakage of said proteinic complexes existing in the tumor cell lines in vitro. The present invention further relates to the use of said peptides for the preparation of a pharmaceutical composition for treating human tumors.

4 Claims, 1 Drawing Sheet

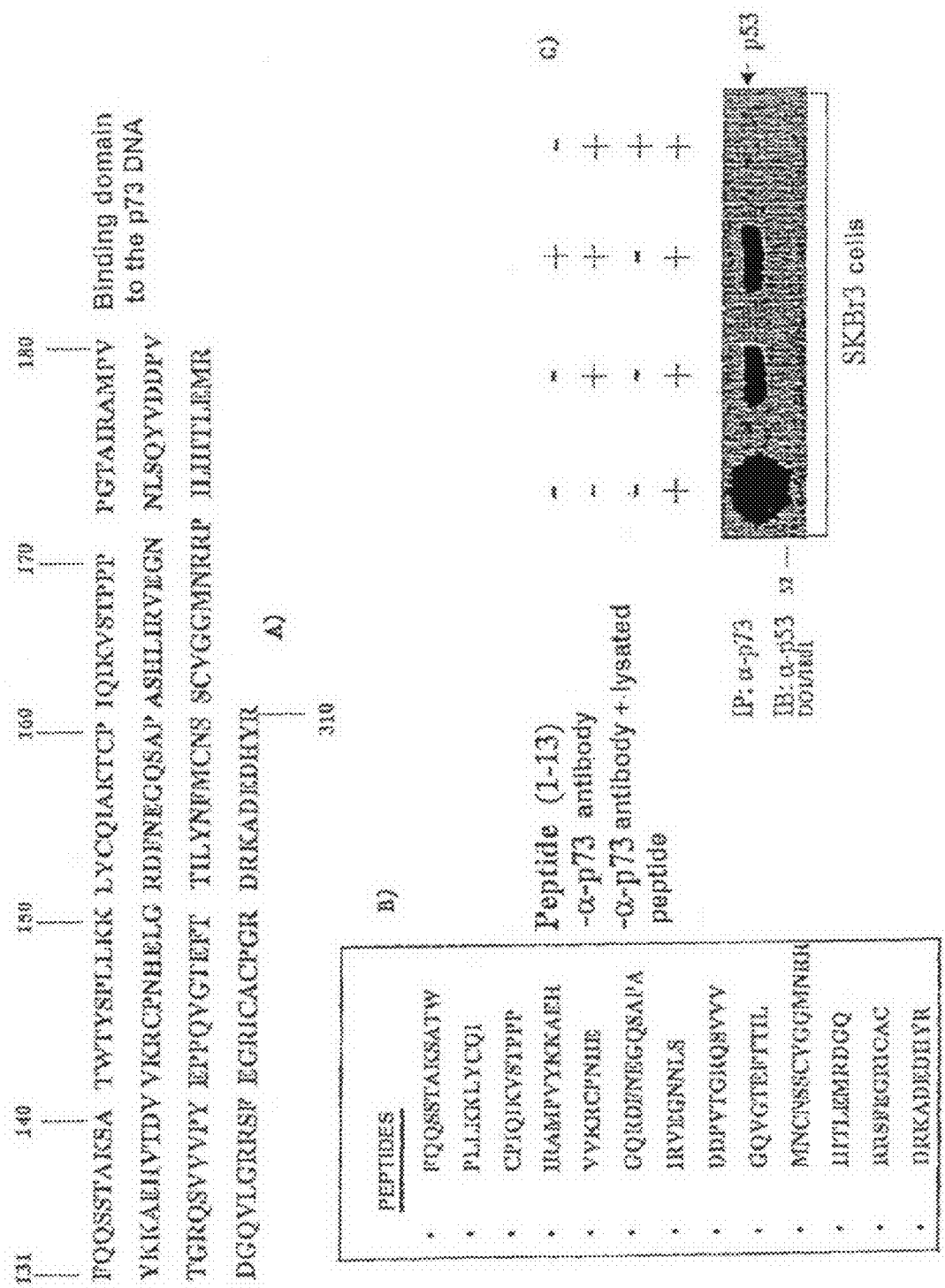

SEQUENCE LISTING

```
<160> NUMBER OF SEQ ID NOS: 14

<210> SEQ ID NO 1
<211> LENGTH: 12
<212> TYPE: PRT
<213> ORGANISM: Artificial
<220> FEATURE:
<223> OTHER INFORMATION: Peptide 1 for use as oncosuppressor

<400> SEQUENCE: 1

Phe Gln Gln Ser Ser Thr Ala Lys Ser Ala Thr Trp
1               5                   10

<210> SEQ ID NO 2
<211> LENGTH: 10
<212> TYPE: PRT
<213> ORGANISM: Artificial
<220> FEATURE:
<223> OTHER INFORMATION: Peptide 2  for use as oncosuppressor

<400> SEQUENCE: 2

Pro Leu Leu Lys Lys Leu Tyr Cys Gln Ile
1               5                   10

<210> SEQ ID NO 3
<211> LENGTH: 12
<212> TYPE: PRT
<213> ORGANISM: Artificial
<220> FEATURE:
<223> OTHER INFORMATION: Peptide 3 for use as oncosuppressor

<400> SEQUENCE: 3

Cys Pro Ile Gln Ile Lys Val Ser Thr Pro Pro Pro
1               5                   10

<210> SEQ ID NO 4
<211> LENGTH: 12
<212> TYPE: PRT
<213> ORGANISM: Artificial
<220> FEATURE:
<223> OTHER INFORMATION: Peptide 4 for use as oncosuppressor

<400> SEQUENCE: 4

Ile Arg Ala Met Pro Val Tyr Lys Lys Ala Glu His
```

```
1               5                   10
```

<210> SEQ ID NO 5
<211> LENGTH: 9
<212> TYPE: PRT
<213> ORGANISM: Artificial
<220> FEATURE:
<223> OTHER INFORMATION: Peptide 5 for use as oncosuppressor

<400> SEQUENCE: 5

```
Val Val Lys Arg Cys Pro Asn His Glu
1               5
```

<210> SEQ ID NO 6
<211> LENGTH: 13
<212> TYPE: PRT
<213> ORGANISM: Artificial
<220> FEATURE:
<223> OTHER INFORMATION: Peptide 6 for use as oncosuppressor

<400> SEQUENCE: 6

```
Gly Gln Arg Asp Phe Asn Glu Gly Gln Ser Ala Pro Ala
1               5                   10
```

<210> SEQ ID NO 7
<211> LENGTH: 9
<212> TYPE: PRT
<213> ORGANISM: Artificial
<220> FEATURE:
<223> OTHER INFORMATION: Peptide 7 for use as oncosuppressor

<400> SEQUENCE: 7

```
Ile Arg Val Glu Gly Asn Asn Leu Ser
1               5
```

<210> SEQ ID NO 8
<211> LENGTH: 12
<212> TYPE: PRT
<213> ORGANISM: Artificial
<220> FEATURE:
<223> OTHER INFORMATION: Peptide 8 for use as oncosuppressor

<400> SEQUENCE: 8

```
Asp Asp Pro Val Thr Gly Arg Gln Ser Val Val Val
1               5                   10
```

<210> SEQ ID NO 9
<211> LENGTH: 11
<212> TYPE: PRT
<213> ORGANISM: Artificial
<220> FEATURE:
<223> OTHER INFORMATION: Peptide 9 for use as oncosuppressor

<400> SEQUENCE: 9

```
Gly Gln Val Gly Thr Glu Phe Thr Thr Ile Leu
1               5                   10
```

<210> SEQ ID NO 10
<211> LENGTH: 14
<212> TYPE: PRT
<213> ORGANISM: Artificial
<220> FEATURE:
<223> OTHER INFORMATION: Peptide 10 for use as oncosuppressor

<400> SEQUENCE: 10

```
Met Asn Cys Asn Ser Ser Cys Val Gly Gly Met Asn Arg Arg
1               5                   10
```

```
<210> SEQ ID NO 11
<211> LENGTH: 11
<212> TYPE: PRT
<213> ORGANISM: Artificial
<220> FEATURE:
<223> OTHER INFORMATION: Peptide 11 for use as oncosuppressor

<400> SEQUENCE: 11

Ile Ile Ile Thr Leu Glu Met Arg Asp Gly Gln
1               5                   10

<210> SEQ ID NO 12
<211> LENGTH: 10
<212> TYPE: PRT
<213> ORGANISM: Artificial
<220> FEATURE:
<223> OTHER INFORMATION: Peptide 12 for use as oncosuppressor

<400> SEQUENCE: 12

Arg Arg Ser Phe Glu Gly Arg Ile Cys Ala
1               5                   10

<210> SEQ ID NO 13
<211> LENGTH: 10
<212> TYPE: PRT
<213> ORGANISM: Artificial
<220> FEATURE:
<223> OTHER INFORMATION: Peptide 13 for use as oncosuppressor

<400> SEQUENCE: 13

Asp Arg Lys Ala Asp Glu Asp His Tyr Arg
1               5                   10

<210> SEQ ID NO 14
<211> LENGTH: 180
<212> TYPE: PRT
<213> ORGANISM: Artificial
<220> FEATURE:
<223> OTHER INFORMATION: Binding Domain to the p73 DNA

<400> SEQUENCE: 14

Phe Gln Gln Ser Ser Thr Ala Lys Ser Ala Thr Trp Thr Tyr Ser Pro
1               5                   10                  15

Leu Leu Lys Lys Leu Tyr Cys Gln Ile Ala Lys Thr Cys Pro Ile Gln
                20                  25                  30

Ile Lys Val Ser Thr Pro Pro Pro Gly Thr Ala Ile Arg Ala Met
            35                  40                  45

Pro Val Tyr Lys Lys Ala Glu His Val Thr Asp Val Val Lys Arg Cys
    50                  55                  60

Pro Asn His Glu Leu Gly Arg Asp Phe Asn Glu Gly Gln Ser Ala Pro
65                  70                  75                  80

Ala Ser His Leu Ile Arg Val Glu Gly Asn Asn Leu Ser Gln Tyr Val
                85                  90                  95

Asp Asp Pro Val Thr Gly Arg Gln Ser Val Val Pro Tyr Glu Pro
                100                 105                 110

Pro Gln Val Gly Thr Glu Phe Thr Thr Ile Leu Tyr Asn Phe Met Cys
            115                 120                 125

Asn Ser Ser Cys Val Gly Gly Met Asn Arg Arg Pro Ile Leu Ile Ile
        130                 135                 140

Ile Thr Leu Glu Met Arg Asp Gly Gln Val Leu Gly Arg Arg Ser Phe
145                 150                 155                 160
```

```
Glu Gly Arg Ile Cys Ala Cys Pro Gly Arg Asp Arg Lys Ala Asp Glu
            165             170                 175

Asp His Tyr Arg
        180
```

PEPTIDE ABLE TO BREAK THE M-P53/P63, M-P53/P73 AND M-P53/RESPECTIVE ISOFORM PROTEINS COMPLEX FORMED IN THE TUMOR CELLS AND USES THEREOF IN THE PHARMACOLOGICAL FIELD

The object of the present invention is the identification of a group of peptides able to break the interaction between the mutated protein p53 (hereinafter m-p53) and the proteins p63, p73 and the respective isoform proteins (hereinafter p63, p73 and p-isoforms) in the m-p53/p63, m-p53/p73 and m-p53/p-isoforms proteinic complex being formed in the nucleus of tumor cells. Furthermore, the present invention relates to a method for causing the breakage of said proteinic complexes existing in the tumor cell lines in vitro. The present invention further relates to the use of said peptides for the preparation of a pharmaceutical composition for the treatment of human tumors.

It is known that the family of the proteins p53 includes the following proteins: p53, p63, p73 and the respective isoforms. All these proteins are involved in the oncosuppression processes through the induction of cell proliferation stopping (apoptosis), differentiation and senescence.

It is known the existence, in tumor cell lines, of m-p53/73 and m-p53/p63 proteinic complexes which involve the proteins m-p53, p73 and p63 and the respective isoforms. The formation of such complexes inhibits the transcriptional and apoptotic activity of the p73, p63 and the respective isoforms, that is it weakens and makes ineffective the antitumor activity of the p73, p63 and the relative isoforms.

Subsequently, it has been shown that the residue at 72 position of the protein m-p53 is determining in the binding to the p73. Subsequently, the domains involved in the interaction between the m-p53 and the p73 have been investigated. The investigation has shown that the two contact surfaces between the m-p53 and the p73 are the "core domain" of the m-p53 and the domain of specific binding to the DNA of p73.

The "core domain" of the m-p53 represents that portion of the molecule where the 90% of the mutations found in the human tumors reside. The result of these mutations is that the m-p53 is not longer able to specifically bind to DNA, which is a required function for performing the antitumor activities specifically carried out from the same protein p53 (hereinafter p53) in a wild configuration (wild type).

Indeed, the p53, if it does not show mutations (and therefore it is in a wild type configuration) plays an activity as an antitumor oncosuppressor. On the contrary, if the p53 shows mutations, 90% of which are present in its core domain, the p53 loses its activity as an oncosuppressor (loss of function) and gains additional activities (gain of function), which promote the trans-formation and the maintenance of the transformed phenotype of a cell.

The core domain of the m-p53 represents a platform of protein-protein interaction, which could account for some tumoral properties of the same m-p53.

The binding of the m-p53 with the p73, p63 or the relative isoforms, to form the m-p53/p73, m-p53/p63 or m-p53/p-isoforms complex, prevents the correct positioning of the p73, p63 or p-isoforms on the regulatory regions of the target genes, that is on those genes which are mediators of the antitumor activities of the p73 and p63.

The reason of this missed or inefficient positioning of the p73 and p63 can be justified in that the surface of specific bonding to the DNA is engaged in the formation of the m-p53/p73 and m-p53/p63 proteinic complex. In a tumor cell, the m-p53 has a remarkably increased half-life parameter (from 2 to 24 hours of increase) with respect to that of the wild type p53 (from 6 to 20 minutes). Such half-life is predominant with respect to that of the p73.

Therefore, there is the need of neutralizing the oncogenic activity exerted by the m-p53. In particular, there is the need of inhibiting the m-p53 from its ability of binding and sequestering the p73 or the p63 with the consequent augmentation/increase of the free quota of p73 and p63. The increase of the free quota of p73 and p63 involves an increase of the antitumor activity exerted by the same proteins p73 and p63.

Moreover, the need of being able to determine the role of the m-p53/p73, m-p53/p63 and m-p53/respective isoforms proteinic complex in the formation, maintaining and in the response to the conventional chemotherapeutic treatments of a tumor remains. In effect, it is a question of adjusting an experimental technique which allows to interfere in the formation of said complexes and measure its effect and its impact on the chemotherapeutic response of a tumor.

The main object of the present invention is to select specific peptides, expressly studied, capable of interacting with the m-p53/p73, m-p53/p63 and m-p53/p-isoforms proteinic complexes by causing the breakage of the relative complexes. The breakage of the proteinic complexes will allow to obtain two effects: the first relating to the increase of the free quota of the proteins p63, p73 and relative isoforms, having antitumor activities; the second relating to the neutralization of the m-p53 released from the complex through the formation of a stable binding between m-p53 and the used peptides.

The Applicant has selected a group of peptides among those representing the whole sequence of the domain of specific binding to the DNA of p73, as it is emerged that the interaction surface of the p73 with the p53 corresponds to the domain of specific binding to the DNA of p73.

The selected peptides are able to compete with the p73, p63 and relative isoforms in the interaction with the m-p53 in the formation of the proteinic complexes.

The peptides have been selected among those which can be drawn on the surface of p73 and not on the surface of m-p53.

In fact, the peptides which can be drawn on the surface of m-p53 would be peptides able to interact with the proteinic complex. From such interaction, the m-p53 would be released, as said peptides would bind with the p73, p63 and the relative isoforms. Consequently, the released m-p53 would increase its oncogenic activity.

On the contrary, the Applicant has drawn the peptides on the contact surface of the p73, as the p73 is not subjected to point mutations and therefore maintains unchanged its conformation. The peptides have been selected from those having a minimum and sufficient domain of the protein p73 in the binding with the m-p53.

The protein p73 consists of 636 amino acids (hereinafter shown by aa) which form 4 regions.

A N-terminal region, which represents the domain of transcriptional activation from 1 to 54.

A central region, which represents the domain of specific binding to the DNA from 131 to 310.

A region called C-terminal domain, which includes the oligomerization domain from 345 to 390.

A region called end portion, whose function is not yet completely known, from 390 to 636.

In order to cover all the central region, which represents the domain of specific binding to the DNA, a group including 13 peptides has been designed. Such peptides have allowed to identify the minimum regions, that is the minimum sequences of amino acids (aa) directly involved in the binding with the m-p53.

The peptides selected by the Applicant are selected from the group consisting of:

| | | |
|---|---|---|
| 1) | FQQSSTAKSATW | (SEQ ID NO: 1) |
| 2) | PLLKKLYCQI | (SEQ ID NO: 2) |
| 3) | CPIQIKVSTPPP | (SEQ ID NO: 3) |
| 4) | IRAMPVYKKAEH | (SEQ ID NO: 4) |
| 5) | VVKRCPNHE | (SEQ ID NO: 5) |
| 6) | GQRDFNEGQSAPA | (SEQ ID NO: 6) |
| 7) | IRVEGNNLS | (SEQ ID NO: 7) |
| 8) | DDPVTGRQSVVV | (SEQ ID NO: 8) |
| 9) | GQVGTEFTTIL | (SEQ ID NO: 9) |
| 10) | MNCNSSCVGGMNRR | (SEQ ID NO: 10) |
| 11) | IIITLEMRDGQ | (SEQ ID NO: 11) |
| 12) | RRSFEGRICAC | (SEQ ID NO: 12) |
| 13) | DRKADEDHYR | (SEQ ID NO: 13) |

The length of the peptide has been established as a function of their pharmacological application. In fact, the peptides having a length between 8 and 10 aa are able to permeate the membrane of the cells by allowing the same peptide to reach the action site in the nucleus.

The peptide must be able to cross the cytoplasmatic membrane and the nuclear membrane.

The peptides have been assayed with co-precipitation experiments. Such experiments allow to check the presence of proteinic complexes in vivo in tumor cell lines.

CO-PRECIPITATION EXPERIMENT

In order to assay the ability of the peptides of breaking the interaction between the m-p53 and the p73, co-precipitation experiments have been carried out using, as a cell model, the cells SKBr3 (Human Breast Cancer) which show good endogenous levels of p73 and of a particular form of m-p53 (p53-HIS 175).

It is known that the H 175 mutation present in the m-p53 plays a key role in the binding between m-p53 and p73, by producing a gain of function in the tumoral oncogenic activity.

In the first step, the 13 peptides have been assayed in a single pool. The lysates derived from the SKBr3 cells have been incubated with the peptides-pool.

The lysates of SKBr3 above mentioned have been immunoprecipitated through specific antibodies fo the protein p73 and have been analyzed with the help of the Western-blot technique with antibodies which specifically revealed the presence of the mutated protein p53.

From the results, it is emerged that all the peptides are able to effectively weaken the interaction of the m-p53/p73, m-p53/p63 and m-p53/respective isoforms proteinic complexes.

For the purpose of individuating the minimum region involved or engaged in the interaction between the protein p73 and the m-p53, the 13 peptides have been divided in three subsets.

The logic followed for creating the three subsets has been that of topographically dividing the specific binding domain of p73 in three subdomains: N-terminal, central and C-terminal.

The three subsets have been again assayed with the coprecipitation technique.

At the end of this experiment, it is emerged that the subset representing th central subdomain is able to break the m-p53/p73 proteinic complex.

Such subset includes some peptides selected from the group including: 5) SEQ ID NO: 5, 6) SEQ ID NO: 6 7) SEQ ID NO: 7 and 8) SEQ ID NO: 8.

Said peptides can hinder the formation of the dimer/s mt-p53/p63 and/or mt-p53/p73 in the region of the domain DNA binding of the human tumor protein p73, that is p53-like transcription factor (NiceProt View of Swiss-Prot:015350).

The selected peptides, called with the numbers 5), 6), 7) and 8) are similar therebetween both with respect to the composition in aa (they consist of acid, basic, hydrophobic and polar aa) and for the molecular weight, all these 4 being formed by a number of aa between 9 to 13 aa.

In detail:

Peptide n. 5): SEQ ID NO: 5, MW=1081.26, pI=8.20.

The peptide corresponds to the 190-198 sequence of the protein.

It is a peptide formed by 9 aa, three of which (V, V, P) are hydrophobic, three are basic (K, R, H), one is acid (E) and two are polar (C, N).

Peptide n. 6): SEQ ID NO: 6, MW=1376.4, pI=4.37.

The peptide corresponds to the 200-211 sequence of the protein, except for the addition of Q at 2 position for synthesis reasons.

It is a peptide formed by 13 aa, four of which (F, A, P, A) are hydrophobic, one is basic (R), two are acid (D, E) and six are polar (G, Q, N, G, Q, S).

Peptide n. 7): SEQ ID NO: 7, MW=1000.1, pI=6.00.

The peptide corresponds to the 215-223 sequence of the protein.

It is a peptide formed by 9 aa, three of which (I, V, L) are hydrophobic, one is basic (R), one is acid (E) and four are polar (G, N, N, S).

Peptide n. 8): SEQ ID NO: 8, MW=1271.3, pI=4.21.

The peptide corresponds to the 227-238 sequence of the protein. It is a peptide formed by 12 aa, 5 of which (P, V, V, V, V) are hydrophobic, one is basic (R), two are acid (D, D) and four are polar (T, G, Q, S).

All the peptides of the present invention are able to inhibit the mt-p53/p63 and/or mt-p53/p73 binding in co-precipitation experiments.

The data obtained from these experiments are summarized in FIG. 1, where it is summarized with: A) the binding domain to the DNA of the protein p73 (SEQ ID NO: 14), B) the synthesized peptides object of the present invention (corresponding to SEQ ID NO:s 1-13) and C) a Western blot experiment.

In FIG. 1 C), the column 1 represents the total cell lysate derived from the SKBr3 cells which is analyzed through western blot using a specific antibody for the protein m-p53. The analysis reveals the presence of good endogenous levels of such protein in the SKBr3 cells. The column 2 represents the total cell lysate derived from the SKBr3 cells which is immunoprecipitated with a specific antibody for the protein p73. The sample is subsequently analyzed through western blot by using the specific antibody for the protein m-p53. The analysis shows, in such a cell context, a good endogenous interaction between the protein p73 and the protein m-p53. The column 3 represents the total cell lysate derived from the SKBr3 cells which is incubated with the pool of peptides, and subsequently is immunoprecipitated with the specific antibody for the protein p73. The sample is then analyzed with western blot with the specific antibody for the protein m-p53. The analysis shows that in the presence of peptides there is a clear increase of protein p53 in respect to the control (column 2). This confirms the ability of the peptides of interacting with the protein m-p53 and the p73 specific antibody. Column 4 represents the total cell lysate derived from the SKBr3 cells which is immunoprecipitated with a mixture constituted by the specific antibody for the protein p73 and the pool of 13 peptides. The sample is subsequently analyzed by western blot by using the specific antibody for the protein m-p53. The analysis shows the ability of the peptides of saturating the antibody for the protein p73 by masking the binding site for the antigen p73.

The synthesis of the peptides has been carried out in solid phase on a Pioneer peptide synthesis system by using the Fmoc technique in order to assemble the chain. In this method, the amino α-group (N$^\alpha$) is provisionally protected by the 9-fluorenilmethoxycarbonyl group (Fmoc). The Fmoc group is an unstable base which can be rapidly removed by a secondary amine, as well as the 20% piperidine in N,N-dimethylformamide. The peptide chain is assembled by reacting the N-terminal unblocked group of an amino acid bound to the solid support with the activated C-terminal carboxy group of the following amino acid through the formation of an amide bond. The activation of the carboxy group alters the electron density around the carboxylated carbon by allowing the nucleophile addition of the N-terminal of the increasing chain on the solid support. There are many chemical activators and the choice depends on different factors; we used 1-hydroxybenzotriazole (HOBt). The unblocking process of the N-terminal group, the activation of the carboxy group and the formation of the binding with the following amino acid is repeated until the peptide of interest is completed. At the end of the synthesis the peptide is detached from the support and deprotected with a mixture of trifluoroacetic acid/anisole/mercaptoethanol, precipitated with cold ether and recovered through centrifugation. The peptide obtained is then purified in HPLC, on a sephasil C8 column, using a linear gradient of water-acetonitrile at pH 3. An aliquote of the obtained sample is hydrolized at 108° C. for at least 24 hours with 6N HCl and analyzed for checking the proper amino acids composition in HPLC with a fluorescence detector.

The invention claimed is:

1. Peptide consisting of an amino acid sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 able to cause the breakage of the m-p53/p63, m-p53/p73 and m-p53/p-isoforms proteinic complex that has formed in the nucleus of tumor cells, for use as an oncosuppressor.

2. Peptide according to claim 1, wherein said peptide consists of an amino acid sequence selected from the group consisting of: SEQ ID NO: 5, SEQ ID NO: 6, SEQ ID NO: 7, and SEQ ID NO: 8.

3. A method of preparing an antitumor formulation for the treatment of human tumors, comprising the steps of: (a) providing a peptide according to claim 1; and (b) using said peptide for the preparation of an antitumor formulation for the treatment of human tumors, wherein the human tumor shows, at a cell level, the m-p53/p63, m-p53/p73 and/or m-p53/p-isoforms proteinic complex.

4. A method for causing the breakage of the m-p53/p63, m-p53/p73 and/or m-p53/p-isoforms proteinic complex, said complex being formed in the nucleus of tumor cells of human tumors in vitro, including the following steps:
- arranging a tumor cell line containing the m-p53/p63, m-p53/p73 and/or m-p53/p-isoforms complex in a culture medium;
- adding to said culture medium at least one of the peptides according to claim 1;
- lysing the cells treated with the peptides and subjecting the same to the coprecipitation;
- checking that the breakage of said proteinic complexes has taken place.

* * * * *